United States Patent
Furukawa et al.

[11] Patent Number: 5,932,466
[45] Date of Patent: Aug. 3, 1999

[54] CREATINE AMIDINOHYDROLASE GENE, A NOVEL RECOMBINANT DNA, AND A PROCESS FOR PRODUCING CREATINE AMIDINOHYDROLASE

[75] Inventors: Keisuke Furukawa; Toshio Ichikawa; Masaru Suzuki; Yasuji Koyama, all of Noda, Japan

[73] Assignee: Kikkoman Corporation, Japan

[21] Appl. No.: 08/947,726

[22] Filed: Oct. 9, 1997

Related U.S. Application Data

[63] Continuation of application No. 08/535,444, Sep. 27, 1995, abandoned.

[30] Foreign Application Priority Data

Sep. 29, 1994 [JP] Japan .................................. 6-235737

[51] Int. Cl.$^6$ .............................. C12N 9/78; C12N 15/63; C12N 1/21; C07H 21/04
[52] U.S. Cl. ................... 435/227; 435/320.1; 435/252.3; 536/23.2
[58] Field of Search ...................... 536/23.2; 435/320.1, 435/252.3, 227

[56] References Cited

U.S. PATENT DOCUMENTS 5,451,520  9/1995  Furukawa et al. ...................... 435/227

FOREIGN PATENT DOCUMENTS 62-205786  9/1987  Japan .

OTHER PUBLICATIONS

English abstract of Laid–Open Japanese Patent Publication 62–205786 (A).
Derwent World Patent Index Acc. No. 87–265079/38.
Derwent World Patent Index Acc. No. 95–225787/30.

*Primary Examiner*—Kawai Lau
*Attorney, Agent, or Firm*—Pennie & Edmonds, LLP

[57] ABSTRACT

The present invention relates to a creatine amidinohydrolase gene coding for the amino acid sequence of SEQ ID NO. 2, a recombinant DNA comprising the creatine amidinohydrolase gene inserted into a vector DNA, and a process for producing creatine amidinohydrolase by culturing a microorganism belonging to the genus Escherichia carrying said recombinant DNA and having the ability to produce creatine amidinohydrolase in medium and then recovering creatine amidinohydrolase from the culture.

According to the present invention, creatine amidinohydrolase can be efficiently produced without adding creatine to medium.

3 Claims, 2 Drawing Sheets

CREATINE AMIDINOHYDROLASE GENE, A NOVEL RECOMBINANT DNA, AND A PROCESS FOR PRODUCING CREATINE AMIDINOHYDROLASE

This is a continuation of application Ser. No. 08/535,444, filed Sep. 27, 1995, now abandoned.

FIELD OF THE INVENTION

The present invention relates to a novel gene for creatine amidinohydrolase useful for quantification of creatine, a novel recombinant DNA containing the same, and a process for producing creatine amidinohydrolase.

BACKGROUND OF THE INVENTION

Creatine amidinohydrolase is an enzyme which catalyzes hydrolysis of creatine into sarcosine and urea. This enzyme can be used as a diagnostic reagent for a wide variety of diseases including kidney diseases to quantify creatine in human serum or urine.

However, the conventional creatine amidinohydrolase is disadvantageous because its stable pH range is limited to pH 4.5–8.5 so that its purification is difficult at pH values higher than pH 8.5, and its high Km value leads to the necessity of a long time to measure a sample.

Under such circumstances, the present inventors found that a novel creatine amidinohydrolase with low Km value stable in high pH range can be obtained from Alcaligenes sp. KS-85 (FERM BP-4487) cultured in medium containing creatine, and they applied a patent for the enzyme (Japanese Patent Application No. 318675/1993).

SUMMARY OF THE INVENTION

To produce creatine amidinohydrolase by genetic engineering, the object of the present invention is to provide a creatine amidinohydrolase gene as a source for production, a recombinant DNA containing said gene, and a process for producing creatine amidinohydrolase by the use of said recombinant DNA.

To achieve the object, the present inventors successfully isolated a creatine amidinohydrolase gene from Alcaligenes and determined its structure. Further, the present inventors obtained a recombinant DNA by inserting the creatine amidinohydrolase gene into a vector DNA to transform a strain belonging to the genus Escherichia, and as a result, they found that creatine amidinohydrolase can be efficiently produced by the resulting transformant in medium without addition of creatine.

That is, the first invention is a novel creatine amidinohydrolase gene coding for the amino acid sequence of SEQ ID No: 2, the second invention is a novel recombinant DNA having the creatine amidinohydrolase gene inserted into a vector DNA, and the third invention is a process for producing creatine amidinohydrolase by culturing bacteria belonging to the genus Escherichia capable of producing creatine amidinohydrolase with said recombinant DNA and then recovering creatine amidinohydrolase from the culture.

DETAILED DESCRIPTION OF THE INVENTION

Hereinafter, the present invention is described in detail.

The creatine amidinohydrolase gene of the present invention can be obtained for example in the following manner. Alcaligenes sp. KS-85 is cultured as described in e.g. Current Protocols in Molecular Biology (Wiley Interscience, 1989), and the bacteria thus cultured are subjected to extraction to prepare genomic DNA.

Alcaligenes sp. KS-85 is a strain which was obtained by screening from soil in Kyoto Prefecture, Japan, and its microbial properties are described below. Most of the microbial properties were identified according to the methods described by Takeharu Hasegawa in "Biseibutsu no Bunrui to Doutei" (Classification and Identification of Bacteria), Tokyo University Press (1975). The present inventors further consulted Berjey's Manual of Determinative Bacteriology, 8th ed. (1974) as reference to classify and identify it.

Microbial Properties of Alcaligenes sp. KS-85

(A) Morphological properties

Observed under a microscope [after cultured for 24 to 48 hours at 30° C. on meat broth agar medium, pH 9.0]

(1) Cell form and size: 0.5 to 1.0×0.5 to 4.0$\mu$ rod-shaped Bacillus.

(2) Motility: motile with surrounding flagella.

(3) Spore: absent.

(4) Gram stainability: negative.

(5) Acid fastness: negative.

(B) Growth states in different media (pH 8.0)

(1) Meat broth agar plate culture

Pale yellow and slightly white round colonies of 2 to 3 mm in diameter occur in 5 days of culture at 30° C. The surface is smooth and glossy like fat with the transparent edge.

(2) Meat broth agar slant culture

In 9 days of stationary culture at 30° C., the microorganism grows to spread on the medium. The microorganism is beige and does not produce any pigment.

(3) Meat broth liquid culture

In 9 days of stationary culture at 30° C., the microorganism grows to form a membrane on the surface of liquid medium while precipitates are formed at the bottom.

(4) Meat broth gelatin culture

In 30 days of stationary culture at 20° C., the microorganism grows on only the top of medium and gelatin is not liquefied.

(5) Litmus milk

In 9 days of stationary culture at 30° C., litmus milk is not solidified or liquefied while alkali is produced in medium to raise the initial pH of medium.

(C) Physiological properties

Most of the following tests were conducted in media adjusted to pH 6.5.

(1) Nitrate reduction: not reduced.
(2) Denitrification: absent. (Nitrite is formed under aerobic conditions.)
(3) MR test: negative.
(4) VP test: negative.
(5) Indole formation: not formed.
(6) Hydrogen sulfide formation: not formed.
(7) Starch hydrolysis: not hydrolyzed.
(8) Citric acid utilization: not utilized.
(9) Utilization of inorganic nitrogen sources: not utilized (nitrate and ammonium salt)
(10) Pigment formation: not formed.
(11) Urease: negative.
(12) Oxidase: positive.
(13) Catalase: positive.
(14) Temperature and pH ranges for growth: 15 to 45° C. and pH 6.0 to 9.0.
(15) Attitude toward oxygen: aerobic.
(16) O-F test (Hugh-Leifson method): Neither oxidation nor fermentation occurs.
(17) Formation of acid and gas from sugar: absent. (The sugars examined are: L-arabinose, D-xylose, D-glucose, D-mannose, D-fructose, D-galactose, maltose, sucrose, lactose, trehalose, D-sorbitol, D-mannitol, inositol, glycerin and starch.)

From the microbial properties described above, the present strain was identified as belonging to the genus Alcaligenes and thus designated Alcaligenes sp. KS-85. This strain has been deposited as FERM BP-4487 with the National Institute of Bioscience and Human-Technology, Agency of Industrial Science and Technology, Japan.

The genomic DNA prepared as described above is then partially digested with a restriction enzyme such as Eco RI and separated by agarose gel electrophoresis to give DNA fragments as Eco RI digests, preferably 2 to 5 kb long. If necessary, these may be further treated with e.g. alkaline phosphatase, purified by techniques known in the art such as phenol extraction and concentrated by techniques including ethanol precipitation, to give purified DNA fragments containing the target creatine amidinohydrolase gene.

As the vector DNA used in the present invention, mention may be made of bacteriophage vector DNA, plasmid vector DNA, etc., and specifically plasmid pUC118 (Takara Shuzo Co., Ltd.) etc. are preferably used. To ligate the Eco RI digest prepared above, it is necessary to digest the plasmid vector with Eco RI (Takara Shuzo Co., Ltd.), and the digest may be precipitated with ethanol if necessary.

The above genomic DNA fragment containing the target gene derived from Alcaligenes is then ligated to the above Eco RI-digested plasmid vector in the presence of a ligase such as T4 DNA ligase (Boehringer Mannheim) whereby a recombinant plasmid DNA is obtained.

This recombinant DNA can be used to transform hosts such as E. coli K12, preferably E. coli JM109 (available from Toyobo), XL-Blue (available from Funakoshi) etc. whereby colonies carrying recombinant DNAs with various gene fragments can be obtained.

The resulting colonies can be screened for those carrying a recombinant DNA with the target creatine amidinohydrolase gene by means of colony hybridization as described in the above-mentioned Current Protocols in Molecular Biology (Wiley Interscience, 1989) where an oligonucleotide prepared by end-labeling the gene fragment obtained in Example 1, item (3), with digoxigenin (Boehringer Mannheim) can be used as the probe.

The resulting recombinant DNA containing the target creatine amidinohydrolase gene can be purified by techniques such as density-gradient CsCl ultracentrifugation etc.

The plasmid DNA thus purified is used for sequencing of the creatine amidinohydrolase gene in the manner as described in Example 1, item (4), and the amino acid sequence encoded by the nucleotide sequence is determined. This amino acid sequence is shown in SEQ ID NO: 2. The gene coding for this determined amino acid sequence is the creatine amidinohydrolase gene of the present invention.

Because the gene-containing recombinant DNA obtained as described above lacks a promoter for expression in E. coli, bacteria transformed with this recombinant DNA produce no creatine amidinohydrolase, and thus it is necessary to prepare creatine amidinohydrolase-producing transformants in the manner described below.

A DNA consisting exclusively of a region coding for creatine amidinohydrolase is obtained in the polymerase chain reaction (abbreviated hereinafter to PCR) using the above purified recombinant plasmid as the template and 2 synthetic oligonucleotide primers consisting of 30 nucleotides coding respectively for 10 amino acids in the N- and C-terminals of the creatine amidinohydrolase gene (C-terminal side is the complementary chain). The DNA thus obtained is inserted into a vector DNA carrying a DNA sequence containing a promoter, operator, ribosome binding site, etc., derived from E. coli lactose operon etc. (see The Operon, p. 227, Cold Spring Harbor Laboratory, 1980). The vector DNA used includes, for example, plasmid DNA, bacteriophage DNA, etc. The recombinant DNA thus constructed is used to transform or transduce hosts such as E. coli K-12, preferably JM109 (Toyobo), XL-Blue (Funakoshi), etc., to give each transformant.

Transformation can be effected by the D. M. Morrison method (Methods in Enzymology, 68, 326–331 (1979)) and transduction by the B. Hohn method (Methods in Enzymology, 68, 299–309 (1979)).

The strain belonging to the genus Escherichia on which the ability to produce creatine amidinohydrolase was conferred as described above can be used to produce creatine amidinohydrolase in the following manner.

The bacteria may be cultured by conventional culture methods in solid medium, preferably in liquid medium.

To culture the bacteria, there is used medium containing one or more nitrogen sources such as yeast extract, peptone, meat extract, corn steep liquor and a soybean or wheat bran exudate, one or more inorganic salts such as potassium dihydrogen phosphate, dipotassium hydrogen phosphate, magnesium sulfate, ferric chloride, ferric sulfate and manganese sulfate, optionally sugars or carbohydrates and vitamins.

The initial pH of medium is adjusted preferably within the range of pH 7 to 9, and the bacteria are cultured for 6 to 24 hours at 30 to 42° C., preferably around 37° C., in submerged culture under aeration with stirring, shake culture, stationary culture, etc. After culture was concluded, conventional recovery means can be used to recover creatine amidinohydrolase from the culture.

The bacteria are separated from the culture by filtration, centrifugation, or the like. Although the bacteria can be used after washed in place of the enzyme, it is preferable to recover creatine amidinohydrolase for example by disrupting the bacteria in ultrasonicator, French press, mill, etc., lysing the cell wall with lytic enzyme such as lysozyme, or extracting the enzyme with a surface active agent such as Triton X-100.

The crude enzyme solution thus obtained can be subjected to conventional methods, preferably a suitable combination of salting-out with ammonium sulfate, precipitation with organic solvent, ion-exchange chromatography, gel filtration chromatography, adsorption chromatography, electrophoresis, etc., to isolate creatine amidinohydrolase.

The physicochemical enzymatic properties of the resulting creatine amidinohydrolase are as follows:

(1) Action 1 mole of creatine is hydrolyzed to form 1 mole of sarcosine and 1 mole of urea.

(2) Substrate specificity

Specific for creatine.

(3) Optimum pH

Figure 1:
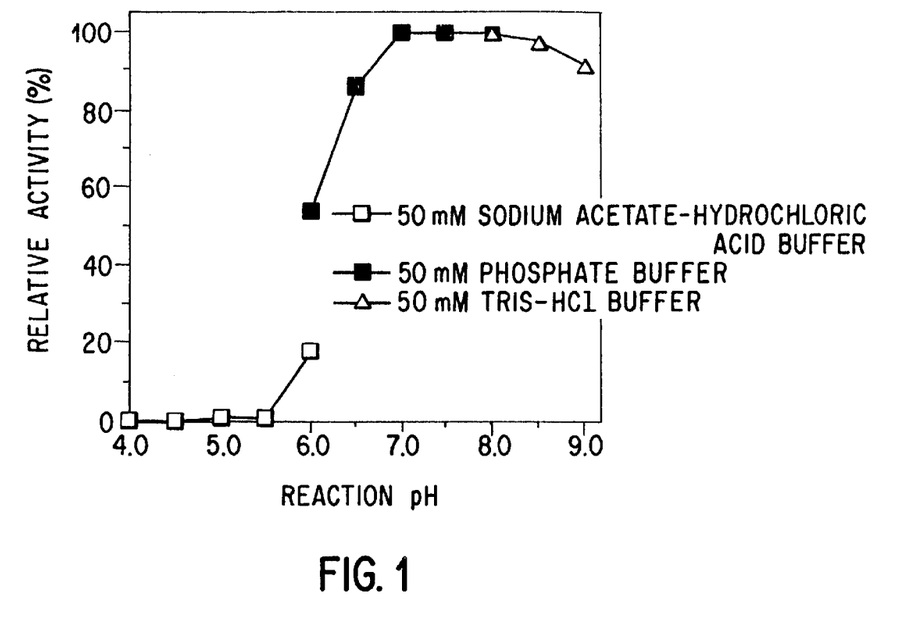
FIG. 1 shows the optimum pH of the creatine amidinohydrolase obtained according to the method of the present invention. Measurement conditions: each pH in corresponding buffer, 37° C., 10 minutes. (The urea formed by enzyme reaction was quantified.)

The activity of the present enzyme was determined at different pH values in 50 mM sodium acetate-hydrochloric acid buffer (pH 4.0 to 6.0), 50 mM phosphate buffer (pH 6.0 to 7.5) and 50 mM Tris-HCl buffer (pH 7.5 to 9.0). As shown in FIG. 1, the result indicated that the optimum pH of the present enzyme is in the range of pH 7.0 to 9.0.

(4) Optimum temperature

Figure 2:
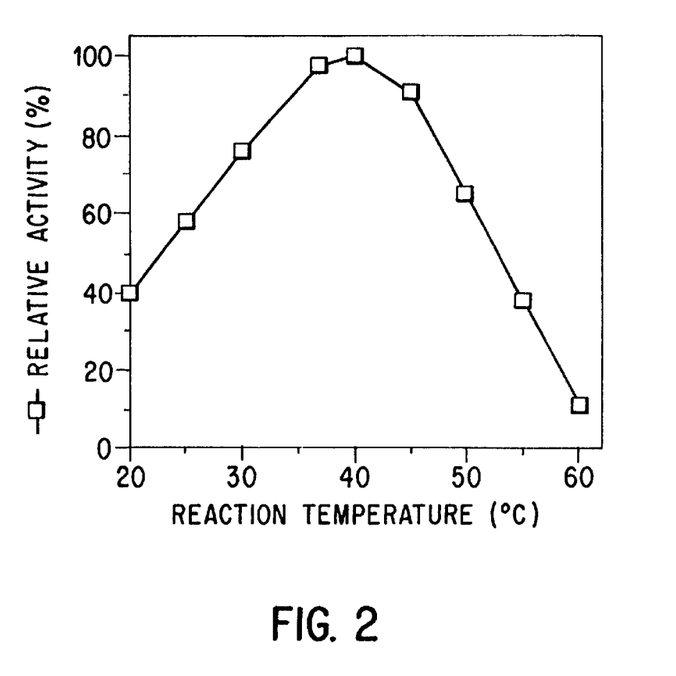
FIG. 2 shows the optimum temperature of the creatine amidinohydrolase obtained according to the method of the present invention. Measurement conditions: 50 mM phosphate buffer, pH 7.7, respective temperatures, 10 minutes. (The urea formed by enzyme reaction was quantified.)

The activity of the present enzyme was determined at different temperatures in the same reaction solutions as in item (7) below. As shown in FIG. 2, the result indicated that the optimum temperature of the present enzyme is in the range of 35 to 45° C.

(5) Stable pH range

Figure 3:
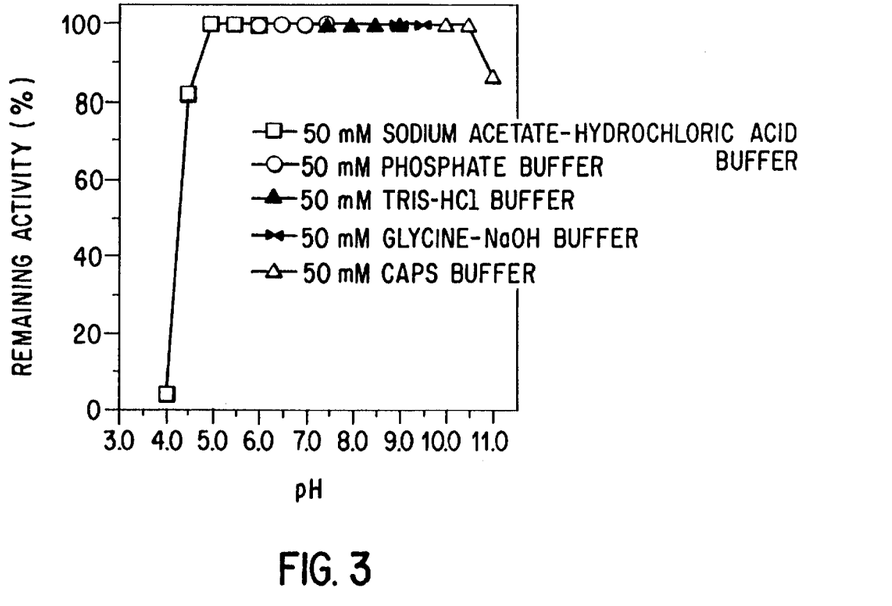
FIG. 3 shows the pH range in which the creatine amidinohydrolase obtained according to the method of the present invention is stable. Treatment conditions: treatment at each pH and 25° C. for 17 hours.

The activity of the present enzyme was determined after treated at different pH values of 4.0 to 11.0 at 25° C. for 17 hours in 50 mM sodium acetate-hydrochloric acid buffer (pH 4.0 to 6.0), 50 mM phosphate buffer (pH 6.0 to 8.0), 50 mM Tris-HCl buffer (pH 8.0 to 9.0), 50 mM glycine-NaOH buffer (pH 9.0 to 10.0) and 50 mM CAPS buffer (pH 10.0 to 11.0). As shown in FIG. 3, the result indicated that the pH range in which the present enzyme is stable is pH 5.0 to 10.5.

(6) Thermal stability

Figure 4:
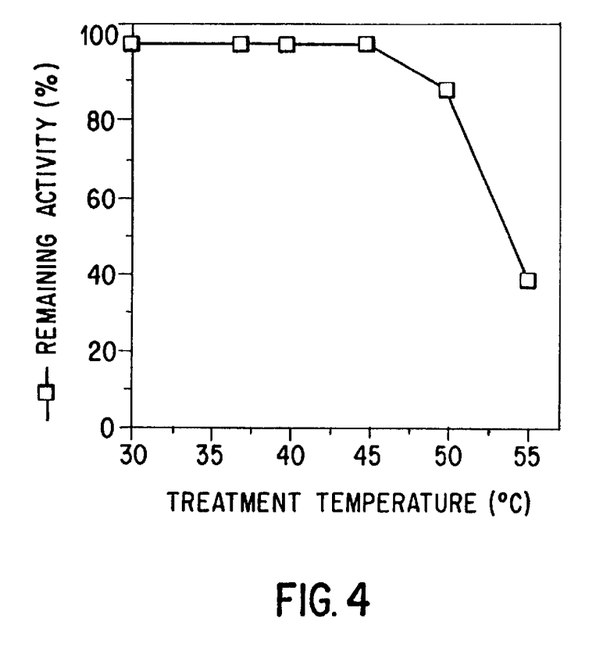
FIG. 4 shows the thermal stability of the creatine amidinohydrolase obtained according to the method of the present invention. Treatment conditions: 50 mM TRIS-HCl buffer, pH 7.5, respective temperatures, 30 minutes. Measurement conditions: 50 mM phosphate buffer, pH 7.7, 37° C., 10 minutes. (The urea formed by enzyme reaction was quantified.)

The enzyme was treated for 30 min. at predetermined temperatures in 50 mM Tris-HCl buffer, pH 7.5. As shown in FIG. 4, the result indicated that the enzyme is stable at temperatures of up to about 45° C.

(7) Method for measurement of enzyme activity

The measurement of enzyme activity was conducted under the following conditions. 1 U of enzyme activity is defined as the amount which causes formation of 1 μmol of urea per minute.

Preparation of reagents

Solution 1 (substrate solution)

6.63 g of creatine is dissolved in 500 ml of 50 mM phosphate buffer, pH 7.7.

Solution 2 (color-producing solution)

10 g of p-dimethylaminobenzaldehyde is dissolved in 500 ml ethanol (guaranteed reagent) and then mixed with a mixture of 575 ml deionized water and 75 ml conc. hydrochloric acid.

Procedures of measurement 1) 0.9 ml of Solution 1 is pre-incubated as the substrate at 37° C. for 5 minutes.

2) 0.1 ml enzyme solution (adjusted to about 1–2 U/ml) is mixed with the substrate and allowed to react at 37° C. for 10 minutes.

3) Then, 2 ml of Solution 2 is mixed with the reaction solution.

4) Then, the mixture is allowed to stand at 25° C. for 20 minutes, and the absorbance at 435 nm is determined (OD sample).

5) As the blank, 0.9 ml of Solution 1 is incubated at 37° C. for 10 minutes and then 2 ml of Solution 2 and 0.1 ml enzyme solution are mixed with Solution 1, and the mixture is allowed to stand at 25° C. for 20 minutes, and the absorbance at 435 nm is determined (OD blank).

Calculation of activity

U/ml=ΔOD×18.06*×dilution degree (18.06* is a coefficient calculated from a urea calibration curve.)

(8) Inhibitors

The effect of each metal salt in Table 1 was examined by adding it to the reaction solution in item (7) above. As shown in Table 1, the result indicated that the present enzyme was strongly inhibited by $AgNo_3$, $HgCl_2$ and $CuSO_4$.

TABLE 1

Result of Inhibition

| inhibitor | final concentration (mM) | relative activity (%) |
|---|---|---|
| (Added to the substrate) | | |
| none | 0 | 100 |
| AgNO3 | 1 | 1 |
| HgCl2 | 1 | 1.9 |
| CuSO4 | 1 | 3.3 |
| (Added to the enzyme solution) | | |
| none | 0 | 100 |
| AgNO3 | 1 | 1 |
| HgCl2 | 1 | 1.7 |
| CuSO4 | 1 | 3.4 |

(9) Km value

The Km value was determined to be $1.3 \times 10^{-2}$M (for creatine) from Lineweaver-Burk plots.

(10) Molecular weight

Gel filtration through a TSK gel G3000SWXL column indicated 80,000±5,000.

EFFECT OF THE INVENTION

According to the present invention, creatine amidinohydrolase can be efficiently produced without adding creatine to medium.

EXAMPLE

The present invention is described in more detail with reference to the following example, which however is not intended to limit the scope of the present invention.

(1) Preparation of genomic DNA from Alcaligenes sp. KS-85

Alcaligenes sp. KS-85 (FERM BP-4487) was inoculated into 200 ml TY medium (1% Bacto-peptone, 0.5% peptone, 0.25% NaCl) and cultured at 30° C. for 20 hours under shaking. The bacteria were collected by centrifuging the culture at 6000 r.p.m. for 10 minutes and then suspended in 25 ml sorbitol solution (0.9M sorbitol, 0.1M Tris-HCl buffer, pH 8.0, 0.1M EDTA). According to Current Protocols in Molecular Biology (Wiley Interscience, 1989), 500 μg genomic DNA was obtained from the suspension.

(2) Preparation of a genomic DNA library

100 μg of the above genomic DNA was partially digested with Eco RI (Takara Shuzo Co., Ltd.) and separated by agarose gel electrophoresis whereby 10 μg of 2 to 5 kb fragments were obtained as Eco RI digest. 1 μg of plasmid vector pUC118 DNA (Takara Shuzo Co., Ltd.) was digested with Eco RI and ligated by the action of 1 unit of T4DNA ligase (Boehringer Mannheim) to 2 μg of the above Eco RI digest of the genomic DNA. According to the D. M. Morrison method (Methods in Enzymology, 68, 326–331, 1979), the resulting plasmid was transformed into *E. coli* JM109 to yield 600 colonies which were then blotted onto a nylon membrane filter Hybond-N+ (a product of Amersham) in the manner described in the manufacture's instructions.

(3) Isolation of the creatine amidinohydrolase gene with colony hybridization

Plasmid vector pLK501 containing a creatine amidinohydrolase gene derived from the genus Flavobacterium (Japanese Laid-Open Patent Publication No. 205786/1987) was partially digested with two restriction enzymes Spl I and Sma I and separated by agarose gel electrophoresis. A portion of the creatine amidinohydrolase gene, 1.2 kb long, was eluted from the gel and further purified with GENECLEAN II (Funakoshi). This gene fragment was end-labeled with digoxigenin using a DIG-labeling kit (Boehringer Mannheim) and used as the probe for colony hybridization. 2 positive colonies were detected by colony hybridization in accordance with Current Protocols in Molecular Biology (WILEY Interscience, 1989).

(4) Analysis of the creatine amidinohydrolase gene

A plasmid DNA containing the target creatine amidinohydrolase gene was separated from one of the above 2 positive colonies by ultracentrifugation and then cleaved with Eco RI. It was found that this Eco RI digest contained an Alcaligenes-derived genomic DNA fragment, approximately 2.5 kb long. Hence, the nucleotide sequence of this plasmid DNA was determined with a Kilo-Sequence deletion kit (Takara Shuzo Co., Ltd.) and 370 DNA Sequencing System (Applied Biosystems). The nucleotide sequence thus determined is set forth in SEQ ID NO: 1 and the amino acid sequence encoded thereby in SEQ ID NO: 2. The creatine amidinohydrolase gene possesses a coding region consisting of 1215 nucleotides encoding 404 amino acids.

(5) Preparation of transformed *E. coli* JM109 (pUCE100)

Expression vector pUTE100 was constructed as described in Japanese Laid-Open Patent Publication No. 317055/1993 as follows. Plasmid vector pBR322 DNA was digested with Eco RI and Nru I, then blunt-ended using a DNA blunting kit (Takara Shuzo Co., Ltd.), separated by agarose gel electrophoresis and purified with GENECLEAN II (Funakoshi) to give an about 3.4 kb DNA fragment containing an origin of replication. This DNA fragment was cyclized by the action of T4 DNA ligase and digested with Eco RI to give a linear fragment as Eco RI digest. Separately, a DNA sequence containing the following expression regulatory region including a promoter, operator, ribosome binding site, etc., derived from *E. coli* lactose operon etc. and an Hpa I restriction site (see The Operon, p. 227, Cold Spring Harbor Laboratory, 1980):

```
AATTCGGTACCGGATCCGCTAGCTTTACATTATGCTTCCGGCTCGTATAATGTGATGCAA    (SEQ ID NO:5)
    GCCATGGCCTAGGCGATCGAAATGTAATACGAAGGCCGAGCATATTACACTACCTT

TTGTGAGCGGATAACAATTCCATCGTTAGGAGGTTTTAGTTAACTAAACTAGTAGA
AACACTCGCCTATTGTTAAGGTAGCAATCCTCCAAAATCAATTGATTTGATCATCT

TCTGGTACCG
AGACCATGGCTTAA
``` was synthesized in DNA Synthesizer Model 392 (Applied Biosystems) and then ligated to the above Eco RI digest, whereby expression vector pUTE100 was obtained.

Then, a region exclusively coding for creatine amidinohydrolase was synthesized by PCR using Geneamp DNA Amplification Reagent Kit with AmpliTaq (Takara Shuzo Co., Ltd.), where the oligonucleotides of SEQ ID NOS: 3 and 4 coding respectively for N- and C-terminal amino acid sequences of creatine amidinohydrolase, synthesized in DNA Synthesizer Model 392 (Applied Biosystems), were used as the primers and the Eco RI digest obtained in item (4) above was used as the template. The resulting fragment was inserted into a Hpa I site of expression plasmid vector pUTE100 DNA obtained above, whereby recombinant plasmid pUCE100 DNA was obtained.

Transformation of *E. coli* JM109 (Toyobo) with recombinant plasmid DNA pUCE100 by the D. M. Morrison method (Methods in Enzymology, 68, 326–331 (1979)) gave a transformant (pUCE100) of *E. coli* JM109. This transformant has been deposited as FERM BP-4803 with the National Institute of Bioscience and Human-Technology, Agency of Industrial Science and Technology, Japan. This transformed *E. coli* JM109 (pUCE100) was cultured under shaking for 16 hours in TY medium (1% Bacto-trypton, 0.5% Bacto-yeast extract, 0.5% NaCl, pH 7.0) containing 1 mM isopropyl-β-D-galactoside. The creatine amidinohydrolase activity evaluated according to the above-described measurement method using a urea calibration curve, was 1.1 U/ml.

What is claimed is:

1. A creatine amidinohydrolase gene coding for the amino acid sequence of SEQ ID NO:2.

2. A recombinant DNA comprising the creatine amidinohydrolase gene of claim 1 inserted into a vector DNA.

3. A process for producing creatine amidinohydrolase, which comprises culturing a microorganism belonging to the genus Escherichia comprising the recombinant DNA of claim 2 and producing creatine amidinohydrolase in the culture medium, and then recovering creatine amidinohydrolase from the culture.

* * * * *

UNITED STATES PATENT AND TRADEMARK OFFICE
CERTIFICATE OF CORRECTION

PATENT NO.    : 5,932,466

DATED         : August 3, 1999

INVENTOR(S)   : FURUKAWA et al.

It is certified that error appears in the above-identified patent and that said Letters Patent is hereby corrected as shown below:

Column 13, line 44 (claim 1, line 1): change "creative" to --creatine--.

Signed and Sealed this

First Day of February, 2000

Attest:

Attesting Officer

Q. TODD DICKINSON

Acting Commissioner of Patents and Trademarks

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
          (A) LENGTH: 1215 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Alcaligenes sp. KS-85
          (B) STRAIN: FERM BP-4487

(xi) SEQUENCE DESCRIPTION: SEQ ID NO:1:

| | | | | | |
|---|---|---|---|---|---|
| ATGACTGACG | ACATGTTGCA | CGTGATGAAA | TGGCACAACG | GCGAAAAAGA | TTATTCGCCG | 60 |
| TTTTCGGATG | CCGAGATGAC | CCGCCGCCAA | AACGACGTTC | GCGGCTGGAT | GGCCAAGAAC | 120 |
| AATGTCGATG | CGGCGCTGTT | CACCTCTTAT | CACTGCATCA | ACTACTATTC | CGGCTGGCTG | 180 |
| TACTGCTATT | TCGGACGCAA | GTACGGCATG | GTCATCGACC | ACAACAACGC | CACGACGATT | 240 |
| TCGGCCGGCA | TCGACGGCGG | CCAGCCCTGG | CGCCGCAGCT | TCGGCGACAA | CATCACCTAC | 300 |
| ACCGACTGGC | GCCGCGACAT | TTTCTATCGC | GCCGTGCGCC | AGCTGACCAC | GGGCGCCAAG | 360 |
| CGCATCGGCA | TCGAGTTCGA | CCACGTCAAT | CTCGACTTCC | GCCGCCAGCT | CGAGGAAGCC | 420 |
| CTACCGGGCG | TCGAGTTCGT | CGACATCAGC | CAGCCCTCGA | TGTGGATGCG | CACCATCAAG | 480 |
| TCGCTCGAAG | AGCAGAAGCT | GATCCGCGAA | GGCGCCCGCG | TGTGTGACGT | CGGCGGCGCG | 540 |
| GCCTGCGCGG | CTGCCATCAA | GGCCGGCGTG | CCCGAGCATG | AAGTGGCGAT | CGCCACCACC | 600 |
| AATGCGATGA | TCCGCGAGAT | CGCCAAATCG | TTCCCCTTCG | TGGAGCTGAT | GGACACCTGG | 660 |
| ACCTGGTTCC | AGTCGGGCAT | CAACACCGAC | GGCGCGCACA | TCCGGTCAC | CAACCGCATC | 720 |
| GTGCAATCCG | GCGACATCCT | TTCGCTCAAC | ACCTTCCCGA | TGATCTTCGG | CTACTACACC | 780 |
| GCGCTGGAGC | GCACGCTGTT | CTGCGACCAT | GTCGATGACG | CCAGCCTCGA | CATCTGGGAG | 840 |
| AAGAACGTGG | CCGTGCATCG | CCGCGGGCTC | GAGCTGATCA | AGCCGGGCGC | GCGCTGCAAG | 900 |
| GACATCGCCA | TCGAGCTCAA | CGAGATGTAC | CGCGAGTGGG | ACCTGCTGAA | GTACCGCTCC | 960 |
| TTCGGCTATG | CCACTCCTT | CGGCGTGCTG | TGCCACTACT | ACGGTCGCGA | GGCGGGCGTG | 1020 |
| GAGCTGCGCG | AGGACATCGA | CACCGAGCTG | AAGCCCGGCA | TGGTGGTCTC | CATGGAGCCG | 1080 |
| ATGGTGATGC | TGCCGGAGGG | CATGCCCGGT | GCCGGCGGCT | ATCGCGAGCA | CGACATCCTG | 1140 |
| ATCGTCGGGG | AGGACGGTGC | CGAGAACATC | ACCGGCTTCC | CGTTCGGTCC | GGAACACAAC | 1200 |
| ATCATCCGCA | ACTGA | | | | | 1215 |

(2) INFORMATION FOR SEQ ID NO:2:

(i) SEQUENCE CHARACTERISTICS:
          (A) LENGTH: 404 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:2:

```
Met Thr Asp Asp Met Leu His Val Met Lys Trp His Asn Gly Glu Lys
1               5                   10                  15

Asp Tyr Ser Pro Phe Ser Asp Ala Glu Met Thr Arg Arg Gln Asn Asp
            20                  25                  30

Val Arg Gly Trp Met Ala Lys Asn Val Asp Ala Ala Leu Phe Thr
        35                  40                  45

Ser Tyr His Cys Ile Asn Tyr Ser Gly Trp Leu Tyr Cys Tyr Phe
50                      55                  60

Gly Arg Lys Tyr Gly Met Val Ile Asp His Asn Asn Ala Thr Thr Ile
65                  70                  75                  80

Ser Ala Gly Ile Asp Gly Gly Gln Pro Trp Arg Arg Ser Phe Gly Asp
                85                  90                  95

Asn Ile Thr Tyr Thr Asp Trp Arg Arg Asp Asn Phe Tyr Arg Ala Val
            100                 105                 110

Arg Gln Leu Thr Thr Gly Ala Lys Arg Ile Gly Ile Glu Phe Asp His
            115                 120                 125

Val Asn Leu Asp Phe Arg Arg Gln Leu Glu Glu Ala Leu Pro Gly Val
            130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Cys Asp
                165                 170                 175

Val Gly Gly Ala Ala Cys Ala Ala Ile Lys Ala Gly Val Pro Glu
                180                 185                 190

His Glu Val Ala Ile Ala Thr Thr Asn Ala Met Ile Arg Glu Ile Ala
            195                 200                 205

Lys Ser Phe Pro Phe Val Glu Leu Met Asp Thr Trp Thr Trp Phe Gln
210                 215                 220

Ser Gly Ile Asn Thr Asp Gly Ala His Asn Pro Val Thr Asn Arg Ile
225                 230                 235                 240

Val Gln Ser Gly Asp Ile Leu Ser Leu Asn Thr Phe Pro Met Ile Phe
                245                 250                 255

Gly Tyr Tyr Thr Ala Leu Glu Arg Thr Leu Phe Cys Asp His Val Asp
            260                 265                 270

Asp Ala Ser Leu Asp Ile Trp Glu Lys Asn Val Ala Val His Arg Arg
            275                 280                 285

Gly Leu Glu Leu Ile Lys Pro Gly Ala Arg Cys Lys Asp Ile Ala Ile
            290                 295                 300

Glu Leu Asn Glu Met Tyr Arg Glu Trp Asp Leu Leu Lys Tyr Arg Ser
305                 310                 315                 320

Phe Gly Tyr Gly His Ser Phe Gly Val Leu Cys His Tyr Tyr Gly Arg
                325                 330                 335

Glu Ala Gly Val Glu Leu Arg Glu Asp Ile Asp Thr Glu Leu Lys Pro
            340                 345                 350

Gly Met Val Val Ser Met Glu Pro Met Val Met Leu Pro Glu Gly Met
            355                 360                 365

Pro Gly Ala Gly Gly Tyr Arg Glu His Asp Ile Leu Ile Val Gly Glu
    370                 375                 380

Asp Gly Ala Glu Asn Ile Thr Gly Phe Pro Phe Gly Pro Glu His Asn
385                 390                 395                 400

Ile Ile Arg Asn
```

(2) INFORMATION FOR SEQ ID NO:3:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "synthetic DNA primer"

(xi) SEQUENCE DESCRIPTION: SEQ ID NO:3:

ATGACTGACG ACATGTTGCA CGTGATGAAA                                    30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA primer"

(xi) SEQUENCE DESCRIPTION: SEQ ID NO:4:

TCAGTTGCGG ATGATGTTGT GTTCCGGACC                                    30

(2) INFORMATION FOR SEQ ID NO:5:

(i) SEQUENCE CHARACTERISTICS:
        (A) LENGTH: 130 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

AATTCGGTAC CGGATCCGCT AGCTTTACAT TATGCTTCCG GCTCGTATAA TGTGATGGAA     60

TTGTGAGCGG ATAACAATTC CATCGTTAGG AGGTTTTAGT TAACTAAACT AGTAGATCTG    120

GTACCGAATT                                                          130